(12) United States Patent  
Loureiro et al.

(10) Patent No.: US 7,608,829 B2  
(45) Date of Patent: Oct. 27, 2009

(54) POLYMERIC COMPOSITE SCINTILLATORS AND METHOD FOR MAKING SAME

(75) Inventors: Sergio Paulo Martins Loureiro, Saratoga Springs, NY (US); James Scott Vartuli, Rexford, NY (US); Brent Allen Clothier, Niskayuna, NY (US); Steven Jude Duclos, Clifton Park, NY (US); Mohan Manoharan, Niskayuna, NY (US); Patrick Roland Lucien Malenfant, Clifton Park, NY (US); Venkat Subramaniam Venkataramani, Clifton Park, NY (US); Clifford Bueno, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/728,400

(22) Filed: Mar. 26, 2007

(65) Prior Publication Data

US 2008/0237470 A1    Oct. 2, 2008

(51) Int. Cl.
*C09K 11/02* (2006.01)
(52) U.S. Cl. ............... 250/361 R; 252/301.4 R
(58) Field of Classification Search ............ 250/361 R, 250/362, 458.1, 459.1; 252/301.4 F, 301.4 H, 252/301.4 P, 301.4 R, 301.4 S, 301.5, 301.6 F, 252/301.6 P, 301.6 R, 301.6 S, 301.16, 301.17, 252/301.18, 301.33
See application file for complete search history.

(56) References Cited

U.S. PATENT DOCUMENTS

| 5,116,559 A | 5/1992 | Dole et al. |
|---|---|---|
| 5,116,560 A | 5/1992 | Dole et al. |
| 5,124,072 A | 6/1992 | Dole et al. |
| 5,230,831 A | 7/1993 | Srivastava |
| 5,242,620 A | 9/1993 | Dole et al. |
| 5,273,681 A | 12/1993 | Srivastava |
| 5,273,732 A | 12/1993 | Srivastava et al. |
| 5,312,612 A | 5/1994 | Srivastava et al. |
| 5,552,082 A | 9/1996 | Srivastava et al. |
| 5,571,451 A | 11/1996 | Srivastava et al. |

(Continued)

FOREIGN PATENT DOCUMENTS

| WO | WO2006038449 A1 | 4/2006 |
|---|---|---|
| WO | WO2006063409 A1 | 6/2006 |
| WO | WO2007016193 A2 | 2/2007 |

OTHER PUBLICATIONS

PCT International Search Report dated Jul. 20, 2009.
Yanbin et al., "Synthesis of $SrAl_2O_4:Eu^{2+}, Dy^{3+}$ phosphors by the coupling route of microemulsion with coprecipitation method", Rare Metals, vol. 25, No. 6, pp. 615-619, Dec. 1, 2006.

*Primary Examiner*—David P Porta
*Assistant Examiner*—David S Baker
(74) *Attorney, Agent, or Firm*—Paul J. DiConza

(57) ABSTRACT

A scintillation detector comprising nano-scale particles of a scintillation compound embedded in a plastic matrix is provided. The nano-scale particles may be made from metal oxides, metal oxyhalides, metal oxysulfides, or metal halides. Methods are provided for preparing the nano-scale particles. The particles may be coated with organic compounds or polymers prior to incorporation in the plastic matrix. A technique for matching the refractive index of the plastic matrix with the nano-scale particles by incorporating nano-scale particles of titanium dioxide is also provided. The scintillator may be coupled with one or more photodetectors to form a scintillation detection system. The scintillation detection system may be adapted for use in X-ray and radiation imaging devices, such as digital X-ray imaging, mammography, CT, PET, or SPECT, or may be used in radiation security detectors or subterranean radiation detectors.

44 Claims, 7 Drawing Sheets

U.S. PATENT DOCUMENTS

| | | | |
|---|---|---|---|
| 5,788,883 A | 8/1998 | Srivastava et al. | |
| 5,882,547 A | 3/1999 | Lynch et al. | |
| 6,036,886 A | 3/2000 | Chhabra et al. | |
| 6,093,347 A | 7/2000 | Lynch et al. | |
| 6,210,605 B1 | 4/2001 | Srivastava et al. | |
| 6,242,520 B1 | 6/2001 | Venkataramani et al. | |
| 6,246,744 B1 | 6/2001 | Duclos et al. | |
| 6,294,800 B1 | 9/2001 | Duggal et al. | |
| 6,298,113 B1 | 10/2001 | Duclos et al. | |
| 6,302,959 B2 | 10/2001 | Srivastava et al. | |
| 6,358,441 B2 | 3/2002 | Duclos et al. | |
| 6,366,033 B1 | 4/2002 | Greci et al. | |
| 6,391,434 B1 | 5/2002 | Duclos | |
| 6,402,987 B1 | 6/2002 | Srivastava et al. | |
| 6,429,583 B1 | 8/2002 | Levinson et al. | |
| 6,436,313 B1 | 8/2002 | Srivastava et al. | |
| 6,469,322 B1 | 10/2002 | Srivastava et al. | |
| 6,501,100 B1 | 12/2002 | Srivastava et al. | |
| 6,515,314 B1 | 2/2003 | Duggal et al. | |
| 6,522,065 B1 | 2/2003 | Srivastava et al. | |
| 6,538,371 B1 | 3/2003 | Duggal et al. | |
| 6,566,808 B1 | 5/2003 | Duggal et al. | |
| 6,580,097 B1 | 6/2003 | Soules et al. | |
| 6,585,913 B2 | 7/2003 | Lyons et al. | |
| 6,596,195 B2 | 7/2003 | Srivastava et al. | |
| 6,613,248 B2 | 9/2003 | Setlur et al. | |
| 6,614,872 B2 | 9/2003 | Bueno et al. | |
| 6,621,211 B1 | 9/2003 | Srivastava et al. | |
| 6,630,077 B2 | 10/2003 | Shiang et al. | |
| 6,685,852 B2 | 2/2004 | Setlur et al. | |
| 6,699,406 B2 | 3/2004 | Riman et al. | |
| 6,700,322 B1 | 3/2004 | Duggal et al. | |
| 6,706,212 B2 | 3/2004 | Venkataramani et al. | |
| 6,707,046 B2 | 3/2004 | Possin et al. | |
| 6,761,837 B2 | 7/2004 | Comanzo et al. | |
| 6,784,432 B2 | 8/2004 | Wieczorek | |
| 6,793,848 B2 | 9/2004 | Vartuli et al. | |
| 6,809,471 B2 | 10/2004 | Setlur et al. | |
| 6,809,781 B2 | 10/2004 | Setlur et al. | |
| 6,844,671 B2 | 1/2005 | Setlur et al. | |
| 6,847,162 B2 | 1/2005 | Duggal et al. | |
| 6,853,131 B2 | 2/2005 | Srivastava et al. | |
| 6,867,536 B2 | 3/2005 | Srivastava et al. | |
| 6,911,251 B2 | 6/2005 | Duclos | |
| 6,936,857 B2 | 8/2005 | Doxsee et al. | |
| 6,939,481 B2 | 9/2005 | Srivastava et al. | |
| 6,979,415 B1 | 12/2005 | Krishna et al. | |
| 6,982,046 B2 | 1/2006 | Srivastava et al. | |
| 7,008,558 B2 | 3/2006 | Vartuli et al. | |
| 7,015,510 B2 | 3/2006 | Srivastava et al. | |
| 7,019,452 B2 | 3/2006 | Srivastava et al. | |
| 7,022,263 B2 | 4/2006 | Comanzo et al. | |
| 7,054,408 B2 | 5/2006 | Jiang et al. | |
| 7,056,451 B2 | 6/2006 | Manivannan et al. | |
| 7,056,849 B2 | 6/2006 | Wan et al. | |
| 7,077,978 B2 | 7/2006 | Setlur et al. | |
| 7,077,980 B2 | 7/2006 | Ramachandran et al. | |
| 7,078,702 B2 | 7/2006 | Ringermacher et al. | |
| 7,084,403 B2 | 8/2006 | Srivastava et al. | |
| 7,094,362 B2 | 8/2006 | Setlur et al. | |
| 7,098,460 B2 | 8/2006 | Lyons et al. | |
| 7,119,488 B2 | 10/2006 | Soules et al. | |
| 7,122,128 B2 | 10/2006 | Comanzo et al. | |
| 7,128,849 B2 | 10/2006 | Setlur et al. | |
| 7,141,794 B2 | 11/2006 | Srivastava et al. | |
| 7,179,402 B2 | 2/2007 | Srivastava et al. | |
| 7,202,477 B2 | 4/2007 | Srivastava et al. | |
| 7,214,947 B2 | 5/2007 | Bueno et al. | |
| 7,218,706 B2 | 5/2007 | Hopkins et al. | |
| 7,224,766 B2 | 5/2007 | Jiang et al. | |
| 7,244,955 B2 | 7/2007 | Bueno et al. | |
| 7,252,789 B2 | 8/2007 | Venkataramani et al. | |
| 7,267,785 B2 | 9/2007 | Srivastava et al. | |
| 7,311,859 B1 | 12/2007 | Loureiro et al. | |
| 2002/0079455 A1* | 6/2002 | Wieczorek | 250/367 |
| 2004/0104347 A1* | 6/2004 | Bross et al. | 250/367 |
| 2004/0238747 A1* | 12/2004 | Dorenbos et al. | 250/361 R |
| 2005/0029495 A1 | 2/2005 | Hubacek et al. | |
| 2005/0087692 A1* | 4/2005 | Romanov et al. | 250/363.03 |
| 2005/0218330 A1 | 10/2005 | Rose et al. | |
| 2006/0018835 A1 | 1/2006 | Malenfant et al. | |
| 2006/0033030 A1* | 2/2006 | Ito et al. | 250/370.11 |
| 2006/0054863 A1* | 3/2006 | Dai et al. | 252/301.4 R |
| 2006/0084566 A1 | 4/2006 | Wan et al. | |
| 2006/0133978 A1 | 6/2006 | Williams et al. | |
| 2006/0214115 A1 | 9/2006 | Manivanna et al. | |
| 2006/0222757 A1 | 10/2006 | Loureiro et al. | |
| 2006/0226368 A1 | 10/2006 | Srivastava et al. | |
| 2006/0231797 A1 | 10/2006 | Riman et al. | |
| 2006/0261722 A1 | 11/2006 | Bueno et al. | |
| 2007/0029493 A1 | 2/2007 | Kniss et al. | |
| 2007/0120298 A1 | 5/2007 | Ku et al. | |
| 2007/0131866 A1 | 6/2007 | Srivastava et al. | |
| 2007/0131874 A1 | 6/2007 | Srivastava et al. | |
| 2007/0257197 A1 | 11/2007 | Gordon et al. | |
| 2007/0281160 A1 | 12/2007 | Krishna et al. | |
| 2007/0284534 A1 | 12/2007 | Srivastava et al. | |
| 2007/0290171 A1 | 12/2007 | Loureiro et al. | |
| 2008/0001087 A1 | 1/2008 | Srivastava et al. | |
| 2008/0011953 A1 | 1/2008 | Srivastava et al. | |
| 2008/0011956 A1* | 1/2008 | Burrell et al. | 250/367 |
| 2008/0093557 A1 | 4/2008 | Cooke et al. | |
| 2008/0241040 A1 | 10/2008 | Clothier et al. | |
| 2008/0241041 A1 | 10/2008 | Clothier et al. | |

* cited by examiner

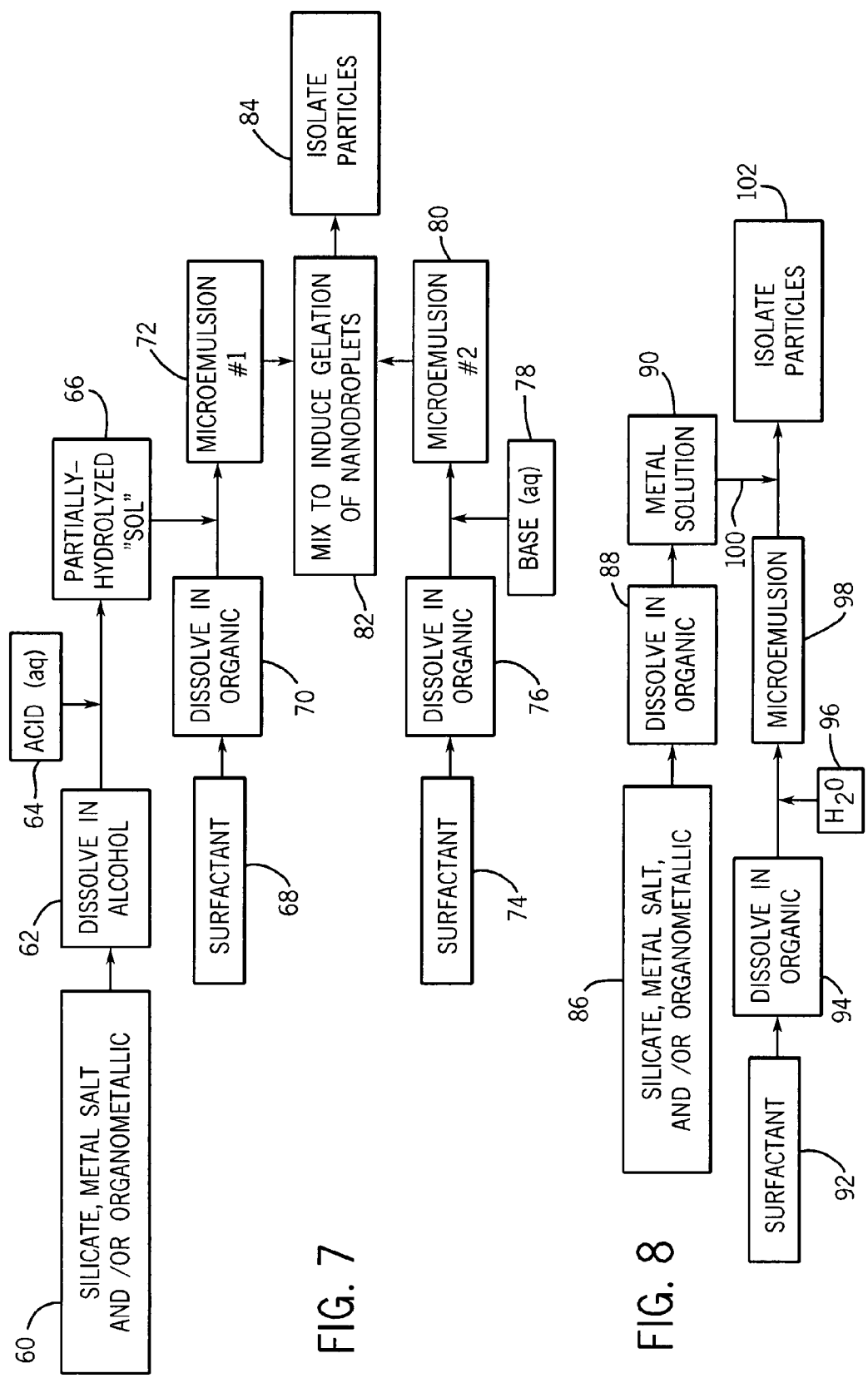

POLYMERIC COMPOSITE SCINTILLATORS AND METHOD FOR MAKING SAME

BACKGROUND

The present invention relates generally to a scintillation material for making scintillation detectors. More specifically, the invention provides a scintillation material comprising nano-scale particles of a metal oxide, a metal oxyhalide, a metal oxysulfide, or a metal halide and methods for preparing the same.

Scintillators are materials that convert high-energy radiation, such as X-rays and gamma rays, into visible light. Scintillators are widely used in detection and non-invasive imaging technologies, such as imaging systems for medical and screening applications. In such systems, high-energy photons typically pass through the person or object undergoing imaging and, on the other side of the imaging volume, impact a scintillator associated with a light detection apparatus. The scintillator typically generates optical photons in response to the high-energy photon impacts. The optical photons may then be measured and quantified by the light detection apparatus, thereby providing a surrogate measure of the amount and location of high-energy radiation incident on the detector. Additionally, scintillators may be useful in systems used to detect radioactive objects, such as contraband or contaminants, which might otherwise be difficult to detect.

With regard to non-invasive imaging techniques, one of the most important applications for scintillators is in medical equipment for the production of radiographic images using digital detection and storage systems. For example, in current digital X-ray imaging systems, such as CT scanners, radiation from a source is directed toward a subject, typically a patient in a medical diagnostic application. A portion of the radiation passes through the patient and impacts a detector. The surface of the detector converts the radiation to light photons which are sensed. The detector is divided into a matrix of discrete picture elements, or pixels, and encodes output signals based upon the quantity or intensity of the radiation impacting each pixel. Because the radiation intensity is altered as the radiation passes through the patient, the images reconstructed based upon the output signals provide a projection of the patient's tissues similar to those available through conventional photographic film techniques.

Another high-energy radiation based imaging system is positron emission tomography (PET), which generally employs a scintillator-based detector having a plurality of pixels typically arranged in a circular array. Each such pixel comprises a scintillator cell coupled to a photomultiplier tube. In PET, a chemical tracer compound having a desired biological activity or affinity is labeled with a radioactive isotope that decays by emitting a positron. Subsequently, the emitted positron interacts with an electron giving out two 511 keV photons (gamma rays). The two gamma rays are emitted simultaneously and travel in opposite directions, penetrate the surrounding tissue, exit the patient's body, and become absorbed and recorded by the detector. By measuring the slight difference in arrival times of the two photons at the two points in the detector, the position of the positron inside the target can be calculated. The limitations of this time difference measurement are highly dependent on the stopping power, light output, and decay time of the scintillator material.

In both CT and PET, a small pixel size is required to generate an accurate image, i.e., for good spatial resolution. To avoid pixel to pixel contamination of the light produced in each luminescent module, the scintillators are made from single crystals or transparent ceramic imaging plates that are cut into small segments, or diced. The smaller segments are used with collimating reflectors between the individual elements to maintain as much of the light toward an individual detector as is physically possible. The dicing process limits the size of the individual pixel, as both production costs and process difficulties increase as the pixel size gets finer.

For systems where a still smaller pixel pitch is required, such as in digital radiographic systems, phosphors such as needles of CsI and fiber optic scintillator (FOS) face plates have been used. However these scintillators do not meet the more stringent luminescence requirements for CT systems. Scintillators based on CsI have a long decay time, leading to afterglow which tends to wash out images. Furthermore, detectors based on FOS plates do not have the high conversion efficiency needed for accurate imaging.

In contrast to the complex scintillators used for imaging applications, scintillators used in the detection of radioactive contraband or contamination are often simple plastic films, made from such materials as polythiophene or polyaniline. However, these systems are not very specific to the type of radiation involved, and often may give false alarms.

Accordingly, there is a need for new scintillators that can be easily formed into materials with the small pixel sizes needed for application in CT and PET, while affording transparency and tailored luminescence properties.

BRIEF DESCRIPTION

In one embodiment, the present techniques provide a scintillator comprising a plastic matrix wherein the plastic matrix comprises embedded nano-scale particles of a scintillation material. In various aspects, the nano-scale particles may be made from metal oxides, metal oxyhalides, metal oxysulfides, metal halides, or combinations thereof.

In another embodiment, the present techniques provide a scintillation detection system comprising a plastic matrix containing embedded nano-scale particles of a scintillation material. One or more photodetectors are attached to the plastic matrix, and are configured to detect photons generated in the plastic matrix.

In another embodiment, the present techniques provide a radiation detection and analysis system comprising a scintillation detection system and a signal processing system, which is configured to analyze the signals generated by the scintillation detection system. The scintillation detection system is made of a scintillator comprising a plastic matrix, containing embedded nano-scale particles of a scintillation material, and an attached light detection apparatus, configured to generate signals in response to photons generated by the scintillator.

In yet another embodiment, the present techniques provide a method for manufacturing a scintillation detector. The method comprises embedding nano-scale particles of a scintillation material in a plastic matrix, and attaching a photodetector system to the plastic matrix. The photodetector system comprises one or more elements configured to convert photons generated in the plastic matrix to electrical signals.

DRAWINGS

These and other features, aspects, and advantages of the present invention will become better understood when the following detailed description is read with reference to the accompanying drawings in which like characters represent like parts throughout the drawings, wherein:

FIG. 7 is a block diagram of a process to make oxide based nano-scale scintillator particles in accordance with embodiments of the current technique.

FIG. 8 is a block diagram of another process to make oxide based nano-scale scintillator particles in accordance with embodiments of the current technique.

DETAILED DESCRIPTION

I. Imaging Systems Using Scintillators

Figure 1:
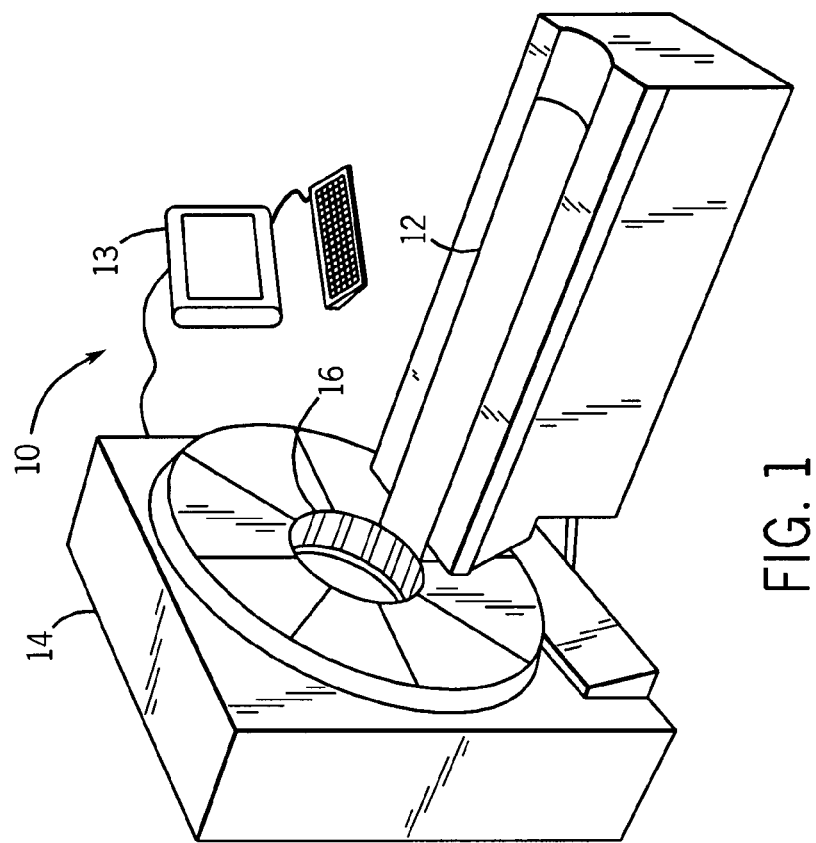
FIG. 1 is a drawing of a medical imaging unit, such as a computed tomography scanner or a positron emission scanner, in which embodiments of the current technique may be used.

Embodiments of the present techniques include new scintillation detectors that may be used for the detection of radiation in imaging systems, security systems, and other devices. For example, FIG. 1 illustrates a medical imaging system 10 in accordance with embodiments of the present technique. This system may be, for example, a positron emission tomography (PET) imaging device, a computer-aided tomography (CT) imaging device, a single positron emission computed tomography (SPECT) system, a mammography system, a tomosynthesis system, or a general X-ray based radiography system, among others. The exemplary system has a frame 14, which contains at least a radiation detector, and may include other equipment, such as a pivoting gantry to move X-ray sources and detectors around the patient. In certain embodiments, the patient is placed on a sliding table 12, and moved through an aperture 16 in the frame 14. In such embodiments, as the patient is moved through the aperture 16, a cross-sectional image of the patient is generated by a data analysis and control system 13. The data analysis system 13 may include multiple units, including calculation, network, and display units. In the case of a CT scanner, the image may be actively generated by pivoting an X-ray source and a detector, contained in the frame 14, around the patient. Alternatively, in PET, SPECT, or other techniques, the image may be passively generated by the detection of emission from a radiation source previously ingested by the patient. In either case, the detector system typically includes a scintillator to absorb high-energy photons, in the form of X-rays or gamma rays, and reemit this energy in the form of visible photons.

Figure 2:
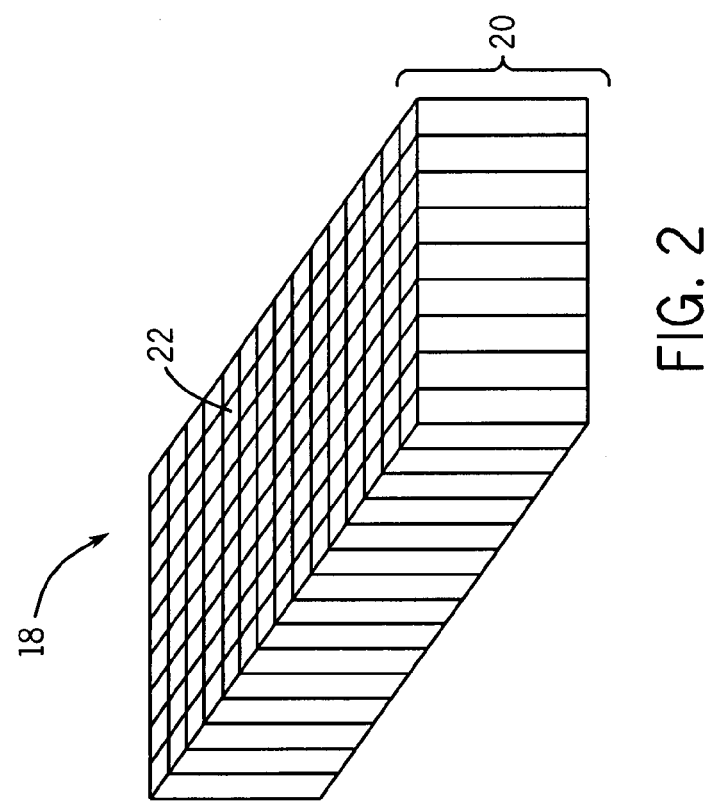
FIG. 2 is a drawing of a detector assembly used in digital imaging systems, such as CT or PET, in which embodiments of the current technique may be used.

An example of a scintillator that may be used in medical imaging systems is shown in FIG. 2. The scintillator 18 may be made from a transparent ceramic material containing a scintillation compound. Alternatively, the scintillator may be made from a large crystal of a radiation sensitive metal halide, such as cesium iodide or another radiation sensitive material. The scintillator assembly 20 typically includes a collection of individual pixels 22, which may be cut from a block of the transparent ceramic or crystalline scintillation material in an operation termed dicing. Once the material is cut into the individual blocks corresponding to pixels, each pixel may be optically isolated from other pixels by a reflector. Furthermore, each pixel may then be joined to an individual photodetector, such as a photodiode, a phototransistor, a photomultiplier tube, a charge-coupled device, or other photoactive device.

Figure 3:
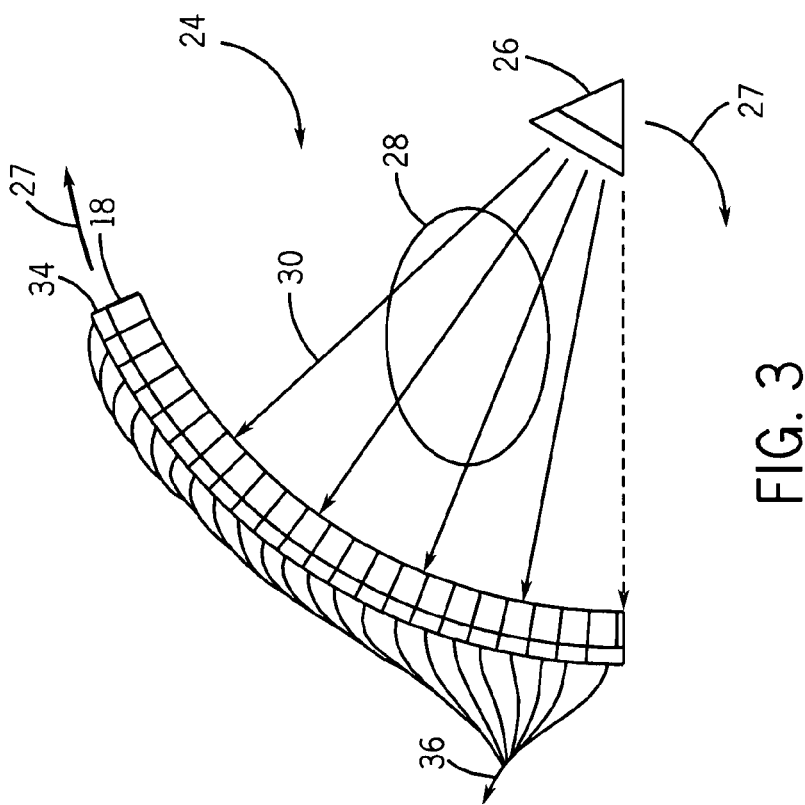
FIG. 3 is a cut away view of an imaging system in which embodiments of the current technique may be used.

The use of such a scintillator is further shown by FIG. 3, which illustrates a scintillation detector assembly 24 from an exemplary imaging system, in this case, a CT system. As shown in this figure, an X-ray source 26 projects a collimated beam of X-rays 30 through a patient 28. As the detector assembly 18, 34 and source 26 are rotated 27 around the patient, the X-rays are attenuated or scattered by structures in the patient 28 prior to impinging on the scintillator 18. In the scintillator 18, many of the high-energy photons of the X-ray beam 30 are absorbed and converted to lower energy visible photons. The visible photons are then detected by a photodetector array 34 attached to the opposite side of the scintillator 18 from the source 26. The photodetector array 34 converts the photons into electric signals, which are carried to the analysis electronics through conductive structures 36. The quality of the image may depend on a number of factors, including the light transmission through the scintillator 18, which controls the amount of light that may reach the photodetectors. Other important factors, specific to the scintillator material, are the amount of high-energy radiation that is absorbed by the scintillator 18, termed the stopping power, and the conversion efficiency, or quantum yield of the scintillator 18. Physical factors also control the image quality, including pixel size and cross-pixel isolation, among others.

II. Scintillators Having Nano-Scale Particles in a Plastic Matrix

Figure 4:
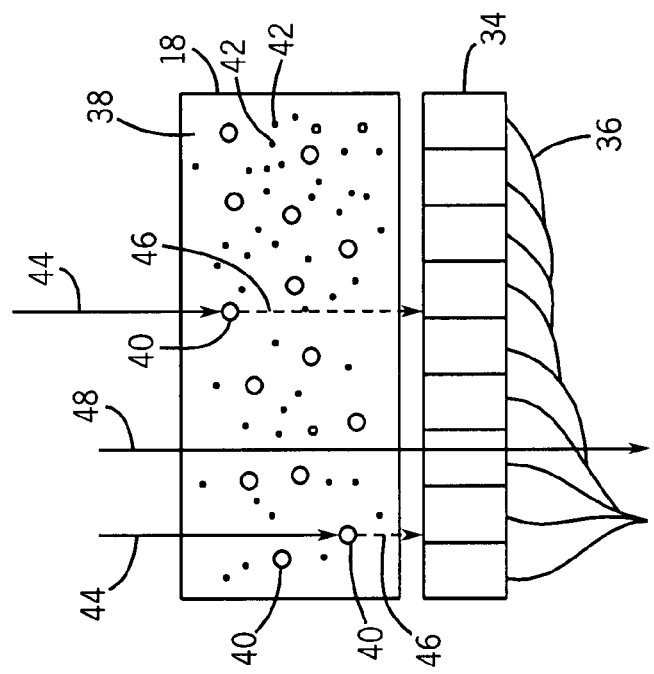
FIG. 4 is a close up view of a scintillation detector system, in accordance with embodiments of the current technique.

FIG. 4 illustrates a scintillator 18 that may be used in a scintillation detector assembly, in accordance with embodiments of the present technique. In this scintillator 18, a plastic matrix 38 contains nano-scale particles 40 of a scintillation material. The plastic matrix 38 may also contain other materials, such as nano-scale particles of materials 42 for refractive index matching, as discussed further below. The nano-scale particles 40 of the scintillation material absorb high-energy photons 44, and reemit the absorbed energy as lower energy photons 46. The lower energy photons 46 may then be captured by the photodetector 34 and converted into electrical signals for transmission back to the analysis system 13 via the conductive structures 36. As discussed above, not all of the energy is captured, with some of the high-energy photons 48 passing through the scintillator 18 and photodetector assembly 34.

A. The Plastic Matrix Material

The plastic matrix 38 may include a large number of materials which transmit light at the frequency of the lower energy photons 46, including both thermoplastic and thermoset materials. In embodiments of the present technique, the matrix may be made from such materials as polycarbonate, polystyrene, polyurethane, polyacrylate, polyamide, polymethylpentene (PMP), cellulose based polymer, styrene-butadiene copolymer, polyethylene terephthalate (PET), polyethylene terephthalate glycol (PETG), or combinations thereof. In other embodiments, the plastic matrix 38 may include such materials as phenol formaldehyde resin, poly N-vinyl carbazole, liquid crystalline polymer (LCP), poly siloxane, polyphosphazene, polyimides, epoxides, phenolic resins, or combinations thereof.

These materials may be formed into the very small pixel sizes that may be needed for specific embodiments by any number of processing techniques. Such techniques may include injection molding, solvent casting, thermoforming, or reactive injection molding, among others. Those skilled in the art will recognize that any other plastic processing technique may be used while remaining within the scope of the present disclosure. Furthermore, the current dicing techniques may also be used to form small pixel assemblies, as the plastic matrix 38 may be more resistant to damage from cutting than currently used materials. In certain embodiments of the present technique, dicing may not be necessary, as the plastic matrix 38 may be an isotropic material, such as a liquid crystalline polymer (LCP). In these matrices, light transmission may be favored or facilitated in certain directions, such as from the front of the scintillator toward the photodetecting components, while being disfavored or inhibited in other directions, such as laterally or side-to-side within the scintillator.

B. Maximizing Light Transmission

In addition to the selection of a transparent plastic matrix 38, light transmission through the scintillator 18 may be maximized in two ways, through the use of nano-scale particles 40 and by matching refractive indices. The nano-scale particles 40 of the scintillation material may be kept as small as possible to avoid scattering light in the scintillator. For example, in some implementations, the particles may be less than about 100 nm in size. Furthermore, the nano-scale particles 40 may be isotropic, or spherical, or they may be anisotropic. If the particles are anisotropic, the relevant size for determination of the scattering is the cross section of the particle perpendicular to the direction of the incoming light. If this cross-section remains low, an anisotropic particle aligned in the direction of the incoming light may be used to increase the conversion efficiency of the system, without significantly decreasing the light transmission.

The second technique for maximizing light transmission is to match the refractive index of the plastic matrix with the refractive index of the scintillation material at the wavelengths of the scintillator emission. Table 1, below, lists the refractive indices for scintillation materials that may be used in exemplary embodiments of the present technique. These values range from 1.8-1.9. In certain embodiments, these refractive indices may be matched by appropriate selection of the matrix material 38. In other embodiments, the refractive indices may be matched by including nano-scale particles of titanium dioxide 42 in the plastic matrix. These particles may be too small to scatter light, and thus, may not interfere with the light transmission through the scintillator. However, the addition of the titanium dioxide particles 42 may increase the refractive index of the plastic matrix. In this embodiment, the refractive index of the plastic matrix 38 may be adjusted to match the refractive index of the nano-scale particles of the scintillation material 40 by controlling the amount of titanium dioxide particles 42 added. In other embodiments, nano-scale particles of tantalum oxide or hafnium oxide may be used for matching the refractive index of the matrix material with the scintillation material. The material used for the nano-scale particles 40 of the scintillation material may be of any compound that has appropriate scintillation properties and is capable of being made into nano-scale particles.

C. Scintillation Materials for Nano-Scale Particles

Materials that may be used in embodiments of the present inventions include metal oxides, metal oxyhalides, metal oxysulfides, or metal halides. For example, in embodiments, the scintillation material may be a metal oxide having the general formulae: $Y_2SiO_5$:Ce; $Y_2Si_2O_7$:Ce; $LuAlO_3$:Ce; $Lu_2SiO_5$:Ce; $Gd_2SiO_5$:Ce; $YAlO_3$:Ce; ZnO:Ga; $CdWO_4$; $LuPO_4$:Ce; $PbWO_4$; $Bi_4Ge_3O_{12}$; $CaWO_4$; $(Y_{1-x}Gd_x)_2O_3$:Eu; $RE_3Al_5O_{12}$:Ce (where RE is at least one rare earth metal); or combinations thereof. In another embodiment the scintillation materials may also include one or more metal oxysulfides, in addition to, or in place of the oxides, such as $Gd_2O_2S$:Tb, or $Gd_2O_2S$:Pr. In other embodiments, the scintillator material may be a metal oxyhalide having a general formula of LaOX:Tb, where X is Cl, Br, or I.

In other embodiments, the scintillator material may be a metal halide having a general formula of $M(X)_n$:Y, wherein M is at least one of La, Na, K, Rb, Cs; each X is independently F, Cl, Br, or I; Y is at least one of Tl, Tb, Na, Ce, Pr, and Eu; and n is an integer between 1 and 4, inclusive. Such phosphors may include, for example, $LaCl_3$:Ce and $LaBr_3$:Ce, among others. In other embodiments, the scintillator material may comprise $[La_{(1-x)}Ce_x][Cl_{(1-y-z)}Br_{(y-z)}I_z]_3$, where x, z, (1-y-z), and (y-z) may range from 0 to 1, instead of, or in addition to the previous phosphors. Other metal halide species that may be used in embodiments of the present invention include $LaCl_3$:Ce, $RbGd_2F_7$:Ce, $CeF_3$, $BaF_2$, CsI(Na), $CaF_2$:Eu, LiI:Eu, CsI, CsF, CsI:Tl, NaI:Tl, and combinations thereof. Halide-like species, such as CdS:In, and ZnS may also be used in embodiments of the present inventions.

The relevant properties of various exemplary scintillation materials are detailed in Table 1, below. These examples are merely provided to illustrate exemplary properties of materials that may be employed as nano-scale scintillation materials and are not intended to limit the scope of the present disclosure. Those skilled in the art will realize that nano-scale particles of other scintillation materials, as described above, may be used while remaining within the scope of the present disclosure.

TABLE 1

Properties of scintillator material candidates for nanopowder synthesis.

| | Light Yield (Photons/MeV) | Emission, Max (nm) | Decay Time (μs) | E/E at 662 KeV (FWHM, %) | Density (g/cm3) | Refractive Index (−) | Hygro-scopic |
|---|---|---|---|---|---|---|---|
| Reference Scintillator | | | | | | | |
| NaI:Tl | 41000 | 410 | 0.23 | 5.6 | 3.67 | 1.85 | highly |
| Oxides - (Y, Gd)$_2$O$_3$:Eu, Y$_2$SiO$_5$, Y$_2$Si$_2$O$_7$ | | | | | | | |
| (Y, Gd)$_2$O$_3$:Eu | >35,000 | 611 | 960 | >10% | 5.95 | 1.9 | no |
| Y2SiO5:Ce | >35000 | 420 | 0.039 | 9.4 | 4.54 | ~1.8 | no |
| Oxyhalides - LaO(Cl, Br, I) | | | | | | | |
| LaOBr:Tb | 67000 | 425 | — | — | ~6.3 | — | Moderately |
| Halides - La(Cl, Br, I)$_3$ | | | | | | | |
| LaCl$_3$:Ce | 49000 | 350 | 0.023 | 3.8 | 3.79 | 1.9 | highly |
| LaBr$_3$:Ce | 63000 | 380 | 0.016 | 2.8 | 5.79 | 1.9 | highly |
| La(Cl$_{0.47}$Br$_{0.53}$)$_3$:Ce | 70000 | 370 | 0.025 | 3.8 | 4.85 | 1.9 | highly |

D. Coating the Nano-Scale Particles

As shown in Table 1, a number of the scintillation materials are moderately to severely hydroscopic, tending to degrade as they absorb water from the atmosphere. Furthermore, nano-scale particles 40 of the scintillation materials may lack compatibility with the plastic matrix 38, leading to agglomeration during processing. Both effects may be lessened by coating the particles 40 prior to incorporation in the matrix. The coating may include either small molecule ligands or polymeric ligands. Exemplary small molecule ligands may include octyl amine, oleic acid, trioctylphosphine oxide, or trialkoxysilane. Those skilled in the art will realize that other small molecule ligands may be used in addition to, or in place of, those listed here. The particles 40 may also be coated with polymeric ligands, which may be either synthesized from the surface of the nano-scale particles 40 or added to the surface of the nano-scale particles 40.

Figure 5:
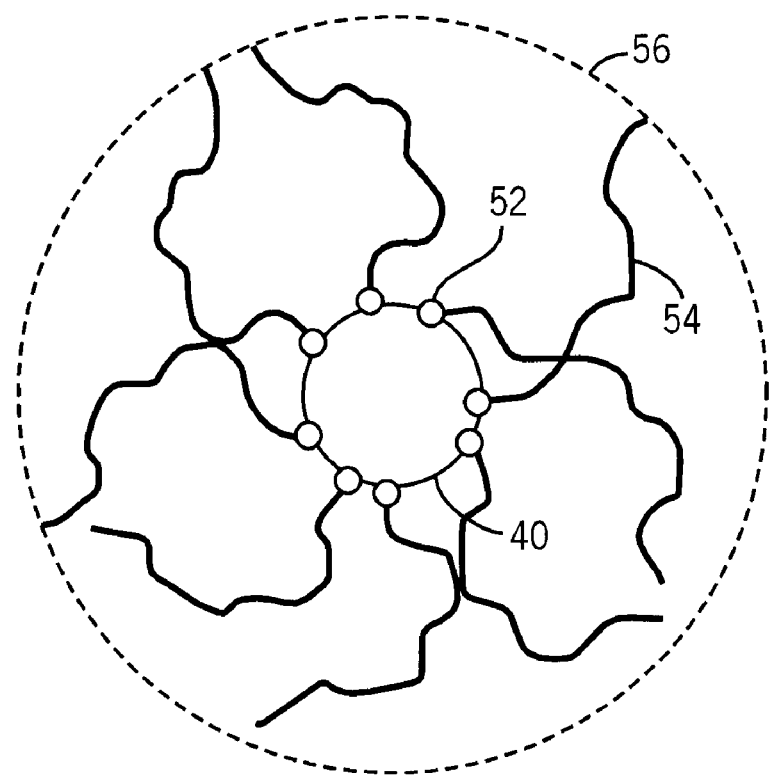
FIG. 5 is a schematic view of a scintillator particle, with adsorbed initiation sites for initiation of a polymerization reaction to form a polymer coating around the particle, in accordance with embodiments of the current technique.

FIG. 5 illustrates an example of coating a particle 40 by growing polymer chains from the surface of the particle 40. In this diagram, the nano-scale particle 40 is functionalized by the addition of polymer initiation compounds to form polymer initiation sites 52 on the particle 40. In certain embodiments, such polymer initiation compounds may include amines, carboxylic acids, or alkoxy silanes, among others. Those skilled in the art will recognize that other polymer initiation compounds may work in addition to, or in place of, those listed here. Once the particle 40 has been functionalized with the initiation compounds, monomers may be added to the solution to grow polymeric or oligomeric chains 54 from the initiation sites 52. The final size of the shell 56 that is formed around the particle 40 will depend on the number of initiation sites 52 and the amount of monomer added to the solution. Those skilled in the art will recognize that these parameters may be adjusted for the results desired.

Figure 6:
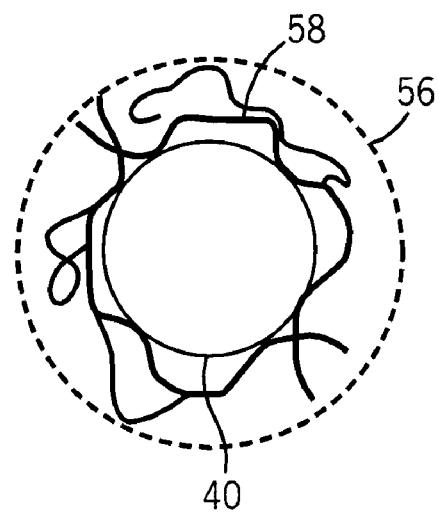
FIG. 6 is a schematic view of a scintillator particle coated with a polymer in accordance with embodiments of the current technique.

FIG. 6 illustrates an example of coating a particle 40 with a polymer 58. In this case, the polymer chain may be chosen to interact with the particle, and may include random copolymers and block copolymers. In the later case, one monomer chain may be chosen to interact with the particle 40, while the other may be chosen to interact with the polymer matrix. In certain embodiments, the polymer coating may include such groups as amines, carboxylic acids, and alkoxy silanes, among others. Those skilled in the art will recognize that other groups may also be effective.

III. Making the Nano-Scale Particles

A number of different procedures may be employed to produce the nano-scale particles 40. For example, nano-scale particles 40 of the metal oxide species described herein may be prepared by the micro-emulsion sol-gel processes detailed with respect to FIGS. 7 and 8, below. Nano-scale particles 40 of metal oxyhalide or oxysulfide species used in other embodiments described herein may be prepared by the processes detailed with respect to FIGS. 9 and 10, below. Furthermore, the nano-scale particles of the metal halide species used in other embodiments described herein may be prepared using ionic liquids, as detailed with respect to FIGS. 11-14, below.

The majority of these processes take advantage of the properties of a micro-emulsion to control the size of the particles. In a micro-emulsion, finely dispersed droplets of a solvent are suspended in another immiscible solvent, such as water in oil. The droplets are stabilized by the addition of an amphiphilic molecule, such as a surfactant, which lowers the interfacial energy between the two incompatible solvents. The amount of the amphiphilic molecule may control the size of the droplets, and the resulting particles. In a water-in-oil configuration, the water droplets are typically sized in the nanometer range, and may be used as reactors to form the final particles. For materials that are sensitive to water, such as the metal halides, micro-emulsions may be formed using an ionic liquid in place of the water.

A. Metal Oxides

FIG. 7 is a block diagram of a sol-gel based micro-emulsion process for the formation of nano-scale particles 40 of a metal oxide scintillation material. In this procedure, a first micro-emulsion 72 is formed by combining an aqueous sol solution 66 with an organic solution 70 containing a surfactant 68.

In this example, the aqueous sol solution 66 is formed by first dissolving one or more silicate compounds, metal salts, and/or organometallics 60 in an alcohol, as shown in block 62. An aqueous acid solution 64 is then added to the alcohol solution to partially hydrolyze the silicate, leading to the formation of the sol solution 66. In an exemplary embodiment, the alcohol used is 1-hexanol. Those skilled in the art will recognize that other alcohols may be employed, such as, for example, straight or branched alkane-based alcohols containing one to ten carbons. In exemplary embodiments, the silicate compounds may be tetraethylorthosilicate (TEOS), tetramethylorthosilicate (TMOS), or combinations thereof. Those skilled in the art will recognize that other silicates may be used for the sol solution precursors. Further, other precursors may be used in addition to, or in place of, silicates to form compounds having different matrices. For example, to form a scintillation compound having an aluminum oxide matrix, aluminum containing compounds may be used, including, for example, triethylaluminum or metal (tetraethyl aluminum), wherein the metal comprises at least one metal anion selected from the group consisting of lanthanoids, group 1 metals, group 2 metals, group 3 metals, group 6 metals, group 12 metals, group 13 metals, group 14 metals, and group 15 metals. In other embodiments, such as, for example, $(Y_{1-x}Gd_x)_2O_3$:Eu or $PbWO_4$, soluble salts of the metals may be used without any added silicate. In cases where metals salts are used without a silicate precursor, an aqueous base may be substituted for the acid 64, to form a partially gelled solution. In this embodiment, base 78 may be omitted from the procedure.

The metal salts chosen depend on the final metal oxide desired. In an exemplary embodiment, the metal salts are $Y(NO_3)_3$ and $Ce(NO_3)_3$. Those skilled in the art will recognize that other metal oxide scintillation materials may be made using this process, which may require that different metal salts be chosen. For example, to manufacture a scintillation compound such as $PbWO_4$, such salts may include $Pb(NO_3)_2$ and $WCl_4$ or $W(OC_2H_5)_6$. Those skilled in the art will recognize that each independent scintillation compound will require the choice of appropriate precursor salts.

The second component of the first micro-emulsion 72 is formed by dissolving a surfactant 68 in an organic solvent as shown in block 70. In an exemplary embodiment, the surfactant is polyoxyethylene (5) nonylphenylether, available as Igepal® CO-520 from ICI Americas. Those skilled in the art will recognize that any number of surfactants may be employed, including such surfactants as aromatic ethoxylates; polyethylene glycol dodecyl ethers, available as Brij® from ICI Americas; sorbitan-fatty acid ester surfactants, available as Tween® from ICI Americas; polyoxyethylenesorbitan fatty acid ester surfactants, available as Span® from ICI Americas; or alkylphenols, among others. In an exemplary embodiment, the organic solvent is n-hexane. Those skilled in the art will recognize that any number of other organic solvents, including alkyl or aryl solvents, may be used.

The second micro-emulsion 80 is formed by dissolving a surfactant 74 in an organic solvent, as shown in block 76, then adding a solution of an aqueous base 78. In an exemplary implementation, the surfactant may be polyoxyethylene (5) nonylphenylether, available as Igepal® CO-520 from ICI Americas. As discussed above, however, any number of other surfactants may be employed while remaining within the scope of the present disclosure. In an exemplary implementation, n-hexane is used as the solvent. Those skilled in the art will recognize that any number of other organic solvents, including alkyl or aryl solvents, may be used. In certain embodiments of the present technique, the aqueous base is ammonium hydroxide. Those skilled in the art will realize that other aqueous base solutions may be employed while remaining within the scope of the present disclosure.

The first micro-emulsion 72 and the second micro-emulsion 80 are combined, as shown in block 82, to form another micro-emulsion containing nano-scale droplets of a sol-gel containing a metal oxide precursor for a scintillation material. The particles of the sol-gel material may be isolated from the combined micro-emulsion, as shown in block 84. In an exemplary implementation, this isolation may be performed by freeze-drying. Those skilled in the art will recognize that other techniques may also be employed to isolate the particles, including pressure filtration and centrifugation, among others. After isolation, the particles may be fired to form the final nano-scale particles of the metal oxide scintillator. This firing is typically performed under a controlled atmosphere at 900-1400° C., for a period of 1 minute to ten hours. Those skilled in the art will recognize that the precise conditions required for firing will depend on the particle size and materials chosen.

FIG. 8 is a block diagram of another procedure for the formation of a metal oxide based scintillator, in accordance with certain embodiments. In this procedure, one or more silicate compounds and one or more organic metal salts 86 are dissolved in an organic solvent, as shown in block 88, to form a silicate/metal salt solution 90. In exemplary embodiments, the silicate compounds may be tetraethylorthosilicate (TEOS), tetramethylorthosilicate (TMOS), or combinations thereof. Those skilled in the art will recognize that other silicates may be used for the sol solution precursors. The metal salts chosen depend on the final metal oxide desired. In an exemplary embodiment, the organic metal salts are yttrium hexanoate or yttrium carboxylate. Those skilled in the art will recognize that other metal oxide scintillation materials, such as those listed previously, may be made using this process, which may require that different metal salts be chosen.

A surfactant 92 is then dissolved in an organic solvent, as shown in block 94. Water 96 is added to this solution to form a micro-emulsion 98. In an exemplary embodiment, the surfactant is polyoxyethylene (5) nonylphenylether, available as Igepal® CO-520 from ICI Americas. Those skilled in the art will recognize that any number of surfactants may be employed, including such surfactants as aromatic ethoxylates; polyethylene glycol dodecyl ethers, available as Brij® from ICI Americas; sorbitan-fatty acid ester surfactants, available as Tween® from ICI Americas; polyoxyethylenesorbitan fatty acid ester surfactant, available as Span® from ICI Americas; or alkylphenols, among others. In an exemplary embodiment, the organic solvent is n-hexane. Those skilled in the art will recognize that any number of other organic solvents, including alkyl or aryl solvents, may be used.

The silicate and/or metal salt solution 90 may be heated and slowly added to the micro-emulsion 98, as indicated by reference numeral 100, to form sol-gel particles containing the metal oxide precursors. As shown in block 102, these particles may be isolated from the micro-emulsion, such as by freeze-drying. Those skilled in the art will recognize that other techniques may also be employed to isolate the particles, including pressure filtration and centrifugation, among others. After isolation, the particles may be fired to form the final nano-scale particles of the metal oxide scintillator. This firing is typically performed under a controlled atmosphere at 900-1400° C., for a period of 1 minute to ten hours. Those skilled in the art will recognize that the precise conditions required for firing will depend on the particle size and materials chosen.

B. Metal Oxyhalides and Oxysulfides

Figure 9:
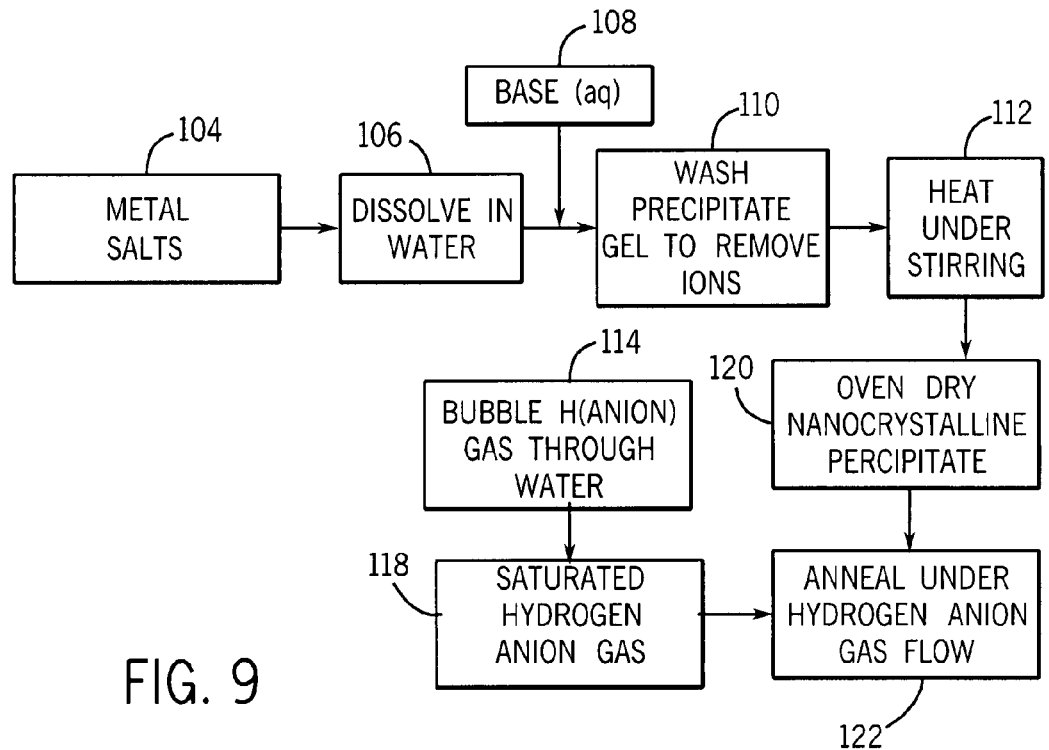
FIG. 9 is a block diagram of a process to make oxyhalide or oxysulfide based nano-scale scintillator particles in accordance with embodiments of the current technique.

A process that may be used to form nano-scale particles of a metal oxyhalide or a metal oxysulfide scintillation material is shown in the block diagram of FIG. 9. In this process, metal salts 104 are dissolved in water, as shown in block 106. In embodiments of the present technique, the metal salts are La(NO$_3$)$_3$ and Ce(NO$_3$)$_3$. Those skilled in the art will recognize that other metal oxyhalide or metal oxysulfide scintillation materials may be made using this process, which may require that different metal salts be chosen. Such metal salts may include metals, and combinations of metals, chosen from groups 2, 3, 13, 14, and 15 of the standard periodic chart. In embodiments of the present technique, the water may either be distilled or otherwise purified to remove ion contamination.

An aqueous base 108 is then added to the water solution to precipitate a gel containing the metal ions. In embodiments of the present technique, the aqueous base is ammonium hydroxide. Those skilled in the art will realize that other aqueous base solutions may be employed while remaining within the scope of the present disclosure. The precipitate gel may be washed to remove excess free ions, as shown in block 110. The gel may be stirred and heated, as shown in block 112, and then oven dried to form a nano-scale crystalline precipitate, as shown in block 120. A hydrogen anion gas, such as, for example, HCl, HBr, or H$_2$S, is bubbled through water, as shown in block 114, to form a saturated solution 118 of the hydrogen anion gas in water. The final metal halide may then be formed by annealing the dried nano-scale crystalline precipitate in an oven under a flow of the water saturated hydrogen anion gas 118, as shown in block 122. In other embodiments, HF or HI may be used with appropriate heating and/or elimination of water. In still other embodiments, the procedure detailed above may be used to form an oxysulfide material, such as, for example, Gd$_2$O$_2$S:Tb or Gd$_2$O$_2$S:Pr. In this embodiment, the gel is formed as described above, and then annealed under a flow of water saturated with H$_2$S to form the final oxysulfide phase. In another embodiment, a metal oxysulfide may be formed by dissolving the metal salt 104, such as, for example, gadolinium nitrate, in propylene carbonate containing tertiary butylsulfide as an emulsifier. The metal salt solution is added to the water 106 to form micelles. The micelles are precipitated by addition of a base 108, and then isolated from the solution and oven dried, as shown in 120. The use of a water saturated hydrogen anion gas flow 122, during the annealing process, may be optional in this embodiment.

Figure 10:
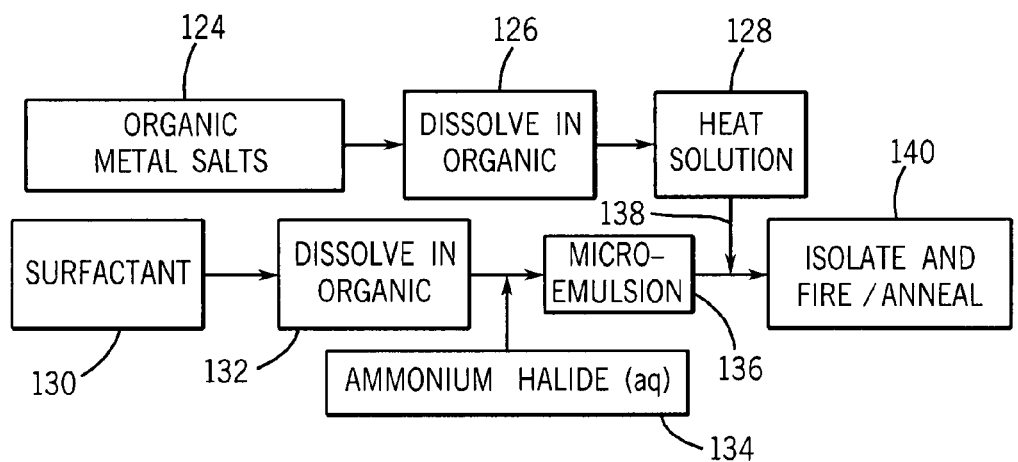
FIG. 10 is a block diagram of another process to make oxyhalide or oxysulfide based nano-scale scintillator particles in accordance with embodiments of the current technique.

An alternate procedure for the formation of a metal oxyhalide or metal oxysulfide is shown by the block diagram in FIG. 10. In this procedure, organic metal salts 124 are dissolved in an organic solvent, as shown in block 126. In embodiments of the present technique, the organic metal salts are La(OR)$_3$ and Ce(OR)$_3$, where R is an alkyl group of one to twelve carbons. Those skilled in the art will recognize that other metal oxyhalide or metal oxysulfide scintillation materials may be made using this process, which may require that different metal salts be chosen. Such metal salts may include metals, and combinations of metals, chosen from the lanthanoids and groups 1, 2, 3, 13, 14, and 15 of the standard periodic chart. In an exemplary embodiment, the organic solvent is n-hexane. Those skilled in the art will recognize that any number of other organic solvents, including alkyl or aryl solvents, may be employed.

A micro-emulsion 136 is prepared by dissolving a surfactant 130, in an organic solvent, as shown in block 132, then adding an ammonium halide 134 to this solution. In embodiments of the present technique, the surfactant is polyoxyethylene (5) nonylphenylether, available as Igepal® CO-520 from ICI Americas. Those skilled in the art will recognize that any number of surfactants may be employed, including such surfactants as aromatic ethoxylates; polyethylene glycol dodecyl ethers, available as Brij® from ICI Americas; sorbitan-fatty acid ester surfactants, available as Tween® from ICI Americas; polyoxyethylenesorbitan fatty acid ester surfactants, available as Span® from ICI Americas; or alkylphenols, among others. In an exemplary embodiment, the organic solvent is n-hexane. Those skilled in the art will recognize that any number of other organic solvents, including alkyl or aryl solvents, may be used. In embodiments of the present technique, the ammonium halide may be NH$_4$Cl, NH$_4$Br, NH$_4$I, NH$_4$F, or combinations thereof.

In other embodiments, the procedure detailed in FIG. 10 may be used to formed oxysulfides, such as, for example, Gd$_2$O$_2$S:Tb or Gd$_2$O$_2$S:Pr. In this embodiment, the starting metal organic salts may include sulfur compounds, wherein one or more of the —OR groups are substituted with —SR groups. An example of such a compound may be Gd(OR)$_2$(SR). Alternatively, a thioacetamide or other sulfur containing species may be used in place of the ammonium halide compound to form the oxysulfide species.

The solution containing the organic metal salts may be heated, as shown in block 128, and then slowly added, as indicated by 138, to the micro-emulsion 136 to form particles of the metal oxyhalide or oxysulfide precursors. As shown in block 140, these particles may be isolated from the micro-emulsion by freeze-drying. Those skilled in the art will recognize that other techniques may be employed to isolate the particles, including pressure filtration and centrifugation, among others.

After isolation, the particles may be fired to form the final nano-scale particles of the metal oxide scintillator. This firing is typically performed under a controlled atmosphere at 900-1400° C., for a period of 1 minute to ten hours. Those skilled in the art will recognize that the precise conditions required for firing will depend on the particle size and materials chosen.

C. Using Ionic Liquids to Make Metal Halides

The procedures for the formation of metal oxide and metal oxyhalide scintillation compounds, discussed above, employ water to form the nano-scale precursors for the scintillators. However, this may not be possible for materials that are sensitive to water, such as metal halide scintillators which are very hydroscopic. Examples of such materials may include NaI:Tl, CsI:Tl, and CsI:Na halide salts. For these materials, micro-emulsions made from ionic liquids and organic solvents may be employed. Ionic liquids represent a new class of strongly-polar, non-aqueous solvents with properties similar to water. For example, the replacement of sodium in NaCl by a bulky imidazolium cation, 1-hexyl-3-methylimidazolium, induces an ionic, salt-like liquid, with a melting point of −75° C., which is capable of substituting for water. This characteristic confers significant advantages in the preparation of hygroscopic materials, allowing the use of common, water-soluble reactants. The ionic liquids may be used to form micro-emulsions, as described for water above, wherein a suspension of nano-scale droplets of an ionic liquid in an organic solvent is stabilized by the addition of a surfactant. The nano-scale droplets may be used as reactors to control the size of the metal halide particles formed.

Potential cations that may be used for ionic liquids are shown below.

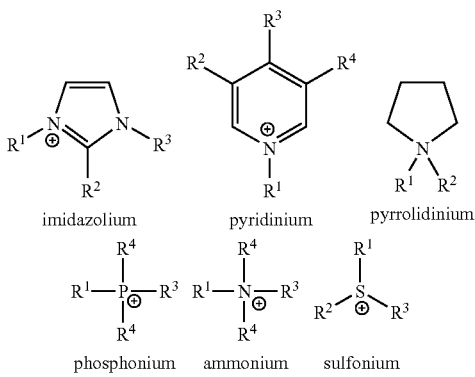

imidazolium  pyridinium  pyrrolidinium phosphonium  ammonium  sulfonium

In these structures, $R^1$-$R^4$ may be an alkyl group, such as —$CH_3$, —$CH_2CH_3$, or —$CH_2CH_2CH_3$, among others. Potential anions that may be used to form an ionic liquid are shown below.

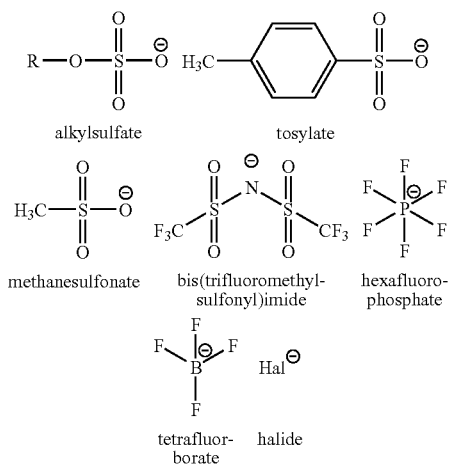

alkylsulfate  tosylate methanesulfonate  bis(trifluoromethyl-sulfonyl)imide  hexafluorophosphate tetrafluoroborate  halide In these structures, R may be an alkyl group, such as —$CH_3$, —$CH_2CH_3$, or —$CH_2CH_2CH_3$, among others. In embodiments of the present technique, ionic liquids that may be employed include imidazolium chloride, or imidazolium bromide, among others. Those skilled in the art will recognize that the choice of the particular anion and cation involved depends on the melting point, dissolution, and other properties desired for the solution.

Figure 11:
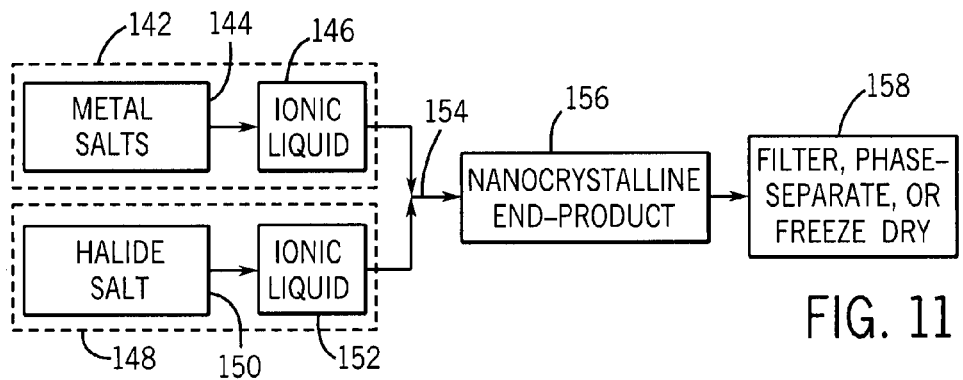
FIG. 11 is a block diagram of a process to make halide based nano-scale scintillator particles in accordance with embodiments of the current technique.

FIG. 11 is a block diagram of a procedure that utilizes ionic liquids to form nano-scale particles of a metal halide, in accordance with embodiments of the present technique. In this procedure, a metal solution 142 is formed by dissolving one or more metal salts 144 in an ionic liquid 146. In embodiments of the present technique, such metal salts may include lanthanum, cerium, rubidium, gadolinium, barium, cesium, calcium, europium, indium, praseodymium, terbium, thallium, and combinations thereof. Those skilled in the art will recognize that this procedure may be used to make nano-scale particles of numerous other metal halide species, and the particular metals chosen will depend on the final product desired. Such metals may include, for example, metals, or combinations of metals, chosen from the lanthanoids, or groups 1, 2, 3, 13, 14, or 15 of the standard periodic chart. The ionic liquid employed may be chosen as discussed above.

A halide solution 148 is prepared by dissolving a halide salt 150 in a second ionic liquid 152. This second ionic liquid may be identical to the first, or a different ionic liquid may be chosen as described above. In embodiments of the present technique the halide salt may be ammonium chloride, ammonium bromide, or a combination thereof. Those skilled in the art will recognize that other halide-type anion source compounds may be used, including materials with a general formula of $NR_4Y$, where each R is independently chosen to be a hydride, alkyl, aryl, or halide, and Y may be a fluoride, chloride, bromide, iodide, or a combination thereof. Further, in other embodiments, other compounds may be used that provide anions that react in similar fashion to halides, such as, for example, sulfur. Such compounds may include, for example, ammonium sulfides, thioacetamides, thioureas, or similar compounds.

The two solutions are combined as indicated by 154 to form the final nano-scale particles 156. The mixing may be done slowly to optimize the particle size formed. Those skilled in the art will recognize that energy may be added during this process to accelerate the reaction, such as by heating, sonication, or other techniques. In embodiments of the present technique, the particles may be isolated from the solution, as shown in block 158, by filtering, phase separation, freeze-drying, or any other technique that may be used to isolate the solid product from the micro-emulsion.

Figure 12:
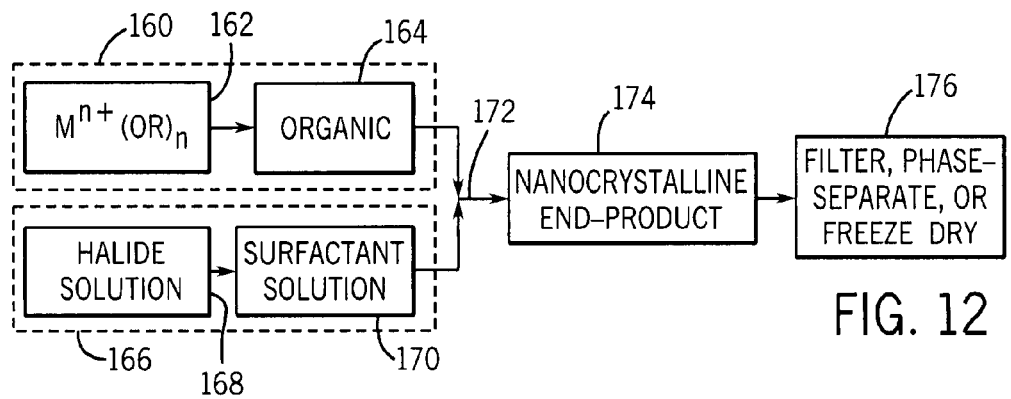
FIG. 12 is a block diagram of another process to make halide based nano-scale scintillator particles in accordance with embodiments of the current technique.

FIG. 12 is a block diagram of another procedure for the formation of nano-scale particles of a metal halide, in accordance with embodiments of the present technique. In this procedure, an organic metal solution 160 is formed by dissolving one or more organic metal salts 162 in an organic solvent 164. In an exemplary embodiment, the organic solvent is n-hexane. Those skilled in the art will recognize that any number of other organic solvents, including alkyl or aryl solvents, may be employed. In embodiments of the present technique, such organic metal salts may include lanthanum, praseodymium, cerium, terbium, thallium, europium, and combinations thereof. Those skilled in the art will recognize that this procedure may be used to make nano-scale particles of numerous other metal halide species, and the particular metals chosen will depend on the final product desired. Such metals may include, for example, metals, or combinations of metals, chosen from the lanthanoids and groups 1, 2, 3, 13, 14, or 15 of the standard periodic chart. The organic anions used to make the metal cations soluble in an organic solution may include one or more independently selected alkoxy groups, —OR, where R represents a carbon chain containing one to ten carbons.

A halide micro-emulsion 166 is then prepared by mixing a halide solution 168 with a surfactant solution 170. The halide solution 168 is prepared using the techniques described above with respect to block 148 in FIG. 11. The surfactant solution 170 is formed by dissolving a surfactant in an organic solvent. In embodiments of the present technique, the surfactant may be polyoxyethylene (5) nonylphenylether, available as Igepal® CO-520 from ICI Americas; aromatic ethoxylates; polyethylene glycol dodecyl ethers, available as Brij® from ICI Americas; sorbitan-fatty acid ester surfactants, available as Tween® from ICI Americas; polyoxyethylenesorbitan fatty acid ester surfactant, available as Span® from ICI Americas; or alkylphenols, among others. In an exemplary embodiment, the organic solvent is n-hexane. Those skilled in the art will recognize that any number of other organic solvents, including alkyl or aryl solvents, may be used.

The organic metal solution 160 is combined with the halide micro-emulsion 166, as indicated by 172, to form the nano-scale particles of the metal halide 174. The mixing may be done slowly to optimize the particle size formed. Those skilled in the art will recognize that energy may be added to accelerate the reaction, such as by heating, sonication, or other techniques. In embodiments of the present technique, the nano-scale particles may be isolated from the solution, as shown in block 176, by filtering, phase separation, freeze-drying, or any other technique that may be used to isolate a solid product from a micro-emulsion.

Figure 13:
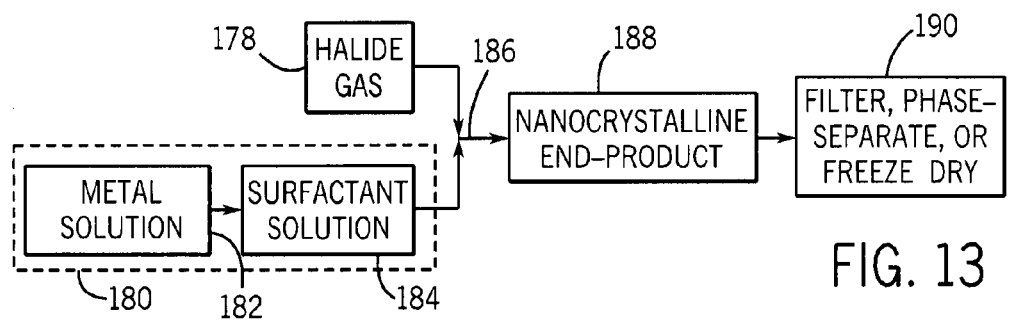
FIG. 13 is a block diagram of yet another process to make halide based nano-scale scintillator particles in accordance with embodiments of the current technique.

FIG. 13 is a block diagram illustrating another technique that may be used to form nano-scale particles of a metal halide, in accordance with embodiments of the present technique. In this procedure a metal micro-emulsion 180 is prepared by mixing a metal solution 182 with a surfactant solution 184. The metal solution 182 is prepared by the techniques described above with respect to block 142 in FIG. 11. The surfactant solution 184 is prepared by the techniques described above with respect to 170 in FIG. 12. A halide gas 178 may then be bubbled through the metal micro-emulsion 180, as indicated by 186, to form the nano-scale particles of the metal-halide 188. In embodiments of the present technique the halide gas may be $Cl_2$, $Br_2$, $F_2$, or, with the addition of heat, $I_2$. Those skilled in the art will recognize that energy may be added during this process to accelerate the reaction, such as by heating, sonication, or other techniques. In embodiments of the present technique, the nano-scale particles may be isolated from the solution, as shown in block 190, by filtering, phase separation, freeze-drying, or any other technique that may be used to isolate a solid product from a micro-emulsion.

Figure 14:
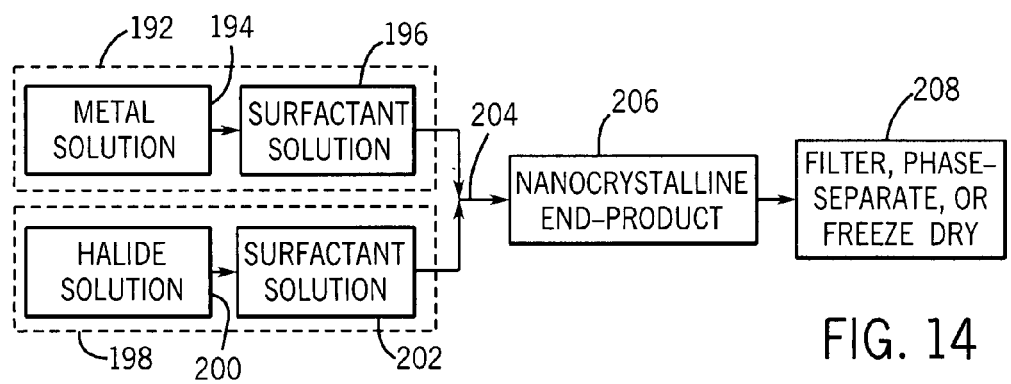
FIG. 14 is a block diagram of yet another process to make halide based nano-scale scintillator particles in accordance with embodiments of the current technique.

FIG. 14 is a block diagram of another process for the formation of a metal halide species in which both the metal and halide precursors are contained in micro-emulsions, in accordance with embodiments of the present technique. The metal micro-emulsion 192 may be prepared by combining a metal solution 194 with a surfactant solution 196, as described above with respect to block 180 in FIG. 13. The halide micro-emulsion 198 may be prepared by the techniques by combining a halide solution 200 with a surfactant solution 202, as described above with respect to block 166 in FIG. 12. The micro-emulsions 192 and 198 are combined, as indicated by 204, to form the nano-scale particles of the metal halide 206. Those skilled in the art will recognize that energy may be added during this process to accelerate the reaction, such as by heating, sonication, or other techniques. In embodiments of the present technique, the nano-scale particles may be isolated from the solution, as shown in block 208, by filtering, phase separation, freeze-drying, or any other technique that may be used to isolate a solid product from a micro-emulsion.

IV. Other Applications

The scintillators of the present technique are not limited to applications in medical imaging devices. Indeed, these devices may by used in any number of structures in which scintillation is necessary for detection of radiation. Examples of such applications are illustrated by FIGS. 15 and 16.

Figure 15:
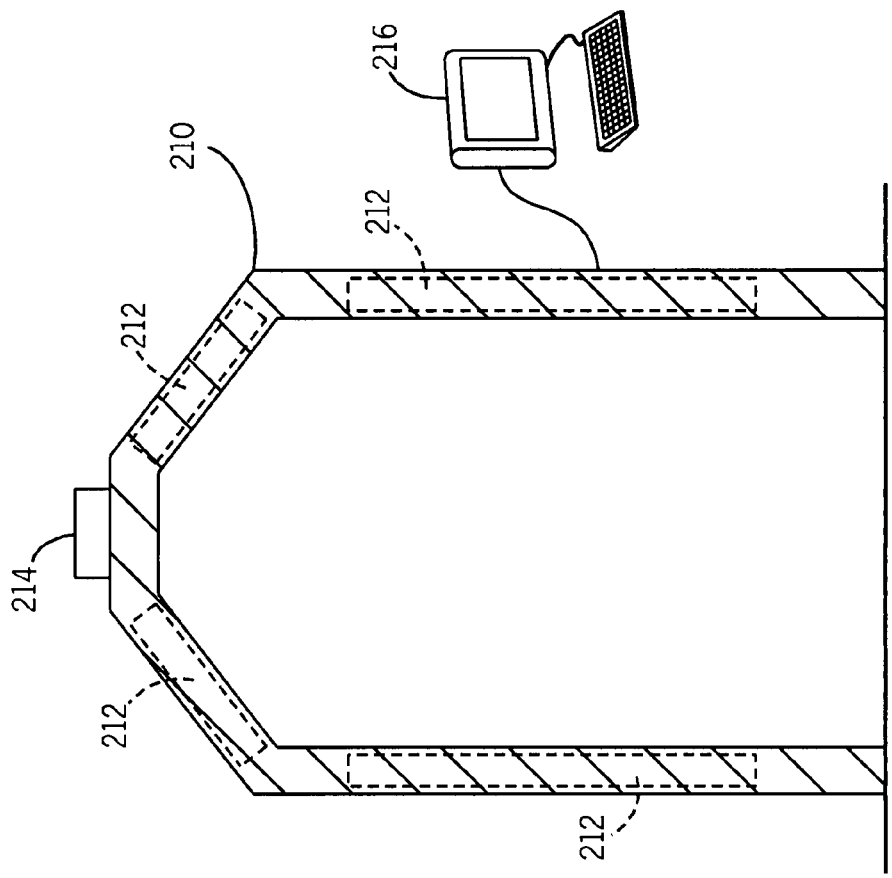
FIG. 15 is a drawing of a security arch used for detecting radioactive contraband in accordance with embodiments of the current technique.
Figure 16:
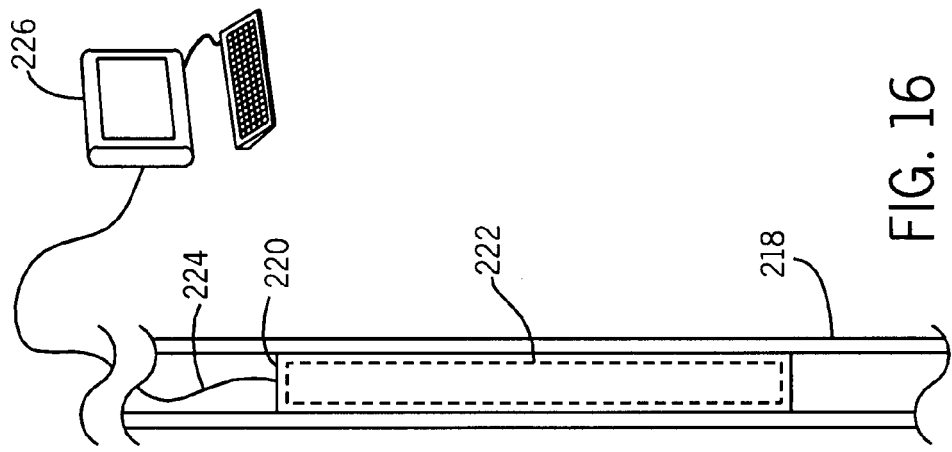
FIG. 16 is a drawing of a radiation detector for detecting subterranean radioactive materials in accordance with embodiments of the current technique.

FIG. 15 is a drawing of a security scanner for the determination of the presence of radioactive contamination or contraband on persons or in items. The scanner includes a frame 210 that may contain one or more scintillation detection assemblies 212. These scintillation detection assemblies 212 may include a plastic matrix containing embedded nano-scale particles of a scintillation material in conjunction with a photodetector, in accordance with embodiments of the present technique. As shown in this illustration, multiple panels may be used to give some idea of the location of the radioactive material within the items passed through the frame 210. In embodiments of the present technique, an alert device 214 may be configured to give a single alarm upon the detection of radioactive materials. In other embodiments, an analysis and control system 216 may be used in addition to, or in place of, the alert device 214, to determine the location or type of contraband detected.

Another application for the scintillators of the present technique is in detectors for determination of subterranean radio-activity. This use is illustrated by the drawing in FIG. 16. In this figure, a well bore 218 has a detector unit 220 that is being lowered through the bore hole. The detector unit 220 contains a scintillation detector assembly 222, which may be made from a plastic matrix containing embedded nano-scale particles of a scintillation material in conjunction with a photo-detector or photodetector array, in accordance with embodiments of the present technique. The detector unit 220 is connected to the surface by a cable 224, which carries the signals from the detector assembly 222 to a signal analysis and control unit 226, located at the surface. The detector unit 220 may be used in oil drilling applications, as well as in other applications, such as prospecting for radioactive materials, among others.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A scintillator comprising:
   a plastic matrix; and
   nano-scale particles of a scintillation material;
   wherein a coating comprising a small molecule ligand is disposed on each nano-scale particle, the ligand comprising trioctylphosphine oxide or trialkoxysilane; and
   wherein the coated nano-scale particles are embedded in the plastic matrix.

2. The scintillator of claim 1 wherein the plastic matrix comprises at least one of an isotropic thermoplastic resin, an anisotropic thermoplastic resin, an isotropic thermoset resin, or an anisotropic thermoset resin.

3. The scintillator of claim 1 wherein the plastic matrix comprises nano-scale particles of at least one of titanium dioxide, zirconium dioxide, tantalum oxide, hafnium oxide, or combinations thereof in an amount sufficient to increase the refractive index of the plastic matrix to match the refractive index of the scintillation material.

4. The scintillator of claim 1 wherein the plastic matrix comprises at least one of polycarbonate, polystyrene, polyurethane, polyacrylate, polyamide, polymethyl pentene, cellulose based polymer, styrene-butadiene copolymer, polyethylene terephthalate (PET), polyethylene terephthalate glycol (PETG), phenol formaldehyde resin, poly N-vinyl carbazole, liquid crystalline polymer (LOP), polysiloxane, polyphosphazene, polyimide, epoxide, phenolic resin, or combinations thereof.

5. The scintillator of claim 1 wherein the nano-scale particles of the scintillator material are less than about 100 nm in size.

6. The scintillator of claim 1 wherein the nano-scale particles of the scintillation material comprise a material selected from the group consisting of metal oxides, metal oxyhalides, metal oxysulfides, metal halides, and combinations thereof.

7. The scintillator of claim 1 wherein the nano-scale particles of the scintillation material comprise at least one phosphor having a general formula of $(Y,Gd)2O3:Eu$; $Y2SiO5:Ce$;

Y2Si2O7:Ce; LuAlO3:Ce; Lu2SiO5:Ce; Gd2SiO5:Ce; YAlO3:Ce; ZnO:Ga; CdWO4; LuPO4:Ce; PbWO4; Bi4Ge3O12; CaWO4; Gd2O2S:Tb; Gd2O2S:Pr; (RE)3Al5O12:Ce, wherein RE is at least one rare earth metal; or combinations thereof.

8. The scintillator of claim 1 wherein the nano-scale particles of the scintillation material comprise at least one phosphor having a general formula of LaOX:Tb; wherein X is selected from the group consisting of Cl, Br, I, and combinations thereof.

9. The method of claim 1 wherein the nano-scale particles of the scintillation material comprise at least one phosphor having the general formula

[La(1-$x$)Ce$x$][Cl(1-$y$-$z$)Br($y$-$z$)I$z$]3; wherein $0 \geq x \geq 1$; $0 \geq (1-y-z) \geq 1$; $0 \geq z \geq 1$; and $0 \geq (y-z) \geq 1$.

10. The method of claim 1 wherein the nano-scale particles of the scintillation material comprise a phosphor having a general formula of MXn:Y; wherein M comprises at least one metal ion selected from the group consisting of La, Na, K, Rb, Cs and combinations thereof; X comprises at least one halide ion selected from the group consisting of F, Cl, Br, I, and combinations thereof; Y comprises at least one metal ion selected from the group consisting of Tl, Tb, Na, Ce, Pr, Eu, and combinations thereof; and n is an integer between 1 and 4, inclusive.

11. The method of claim 1 wherein the nano-scale particles of the scintillation material comprise at least one phosphor having a general formula of LnX3:Ce, wherein each X is independently Cl, Br, or I; RbGd2F7:Ce; CeF3, BaF2, CsI(Na), CaF2:Eu, LiI:Eu, OsI, CsF, CsI:Tl, NaI:Tl, CdS:In, ZnS, or combinations thereof.

12. A scintillation detection system comprising:
a plastic matrix;
nano-scale particles of a scintillation material, wherein a coating comprising a small molecule ligand is disposed on each nano-scale particle, the ligand comprising trioctylphosphine oxide or trialkoxysilane, and wherein the coated nano-scale particles are embedded in the plastic matrix; and
one or more photodetectors attached to the plastic matrix, wherein the one or more photodetectors are configured to detect photons generated in the plastic matrix.

13. The scintillation detection system of claim 12 wherein the plastic matrix comprises at least one of an isotropic thermoplastic resin, an anisotropic thermoplastic resin, an isotropic thermoset resin, or an anisotropic thermoset resin.

14. The scintillation detection system of claim 12 wherein the plastic matrix comprises nano-scale particles of titanium dioxide in a sufficient amount to increase the refractive index of the plastic matrix to match the refractive index of the scintillation material.

15. The scintillation detection system of claim 12 wherein the nano-scale particles of the scintillation material comprise a material selected from the group consisting of metal oxides, metal oxyhalides, metal oxysulfides, metal halides, and combinations thereof.

16. The scintillation detection system of claim 12 wherein the plastic matrix is formed into separate cells and wherein each of the separate cells is attached to a corresponding photodetector.

17. The scintillation detection system of claim 12 wherein the plastic matrix is cut into separate cells and wherein each of the separate cells is attached to a corresponding photodetector.

18. The scintillation detection system of claim 12 wherein the plastic matrix is isotropic and the isotropic alignment of the plastic matrix generally directs light from the nano-scale particles of the scintillation material toward the one or more photodetectors attached to the plastic matrix.

19. The scintillation detection system of claim 12 wherein the plastic matrix is isotropic and the isotropic alignment of the plastic matrix generally suppresses light transmission in a substantially horizontal direction relative to the surfaces of the one or more photodetectors.

20. The scintillation detection system of claim 12 wherein the one or more photodetectors comprise at least one of photomultiplier tubes, photodiodes, phototransistors, or charge coupled array devices.

21. A radiation detection and analysis system comprising:
a scintillation detection system comprising:
a scintillator including:
a plastic matrix; and
nano-scale particles of a scintillation material, wherein a coating comprising a small molecule ligand is disposed on each nano-scale particle, the ligand comprising trioctylphosphine oxide or trialkoxysilane, and wherein the coated nano-scale particles are embedded in the plastic matrix;
a light detection apparatus attached to the scintillator and configured to generate signals in response to photons generated by the scintillator; and
a signal processing system configured to analyze the signals generated by the scintillation detection system.

22. The radiation detection and analysis system of claim 21 wherein the radiation detection and analysis system comprises one of a positron emission tomography (PET) imaging device, a computer-aided tomography (CT) imaging device, a single positron emission computed tomography (SPECT) system, a mammography system, a tomosynthesis system, or a general X-ray based radiography system.

23. The radiation detection and analysis system of claim 21 wherein the radiation detection and analysis system comprises a security scanner for the detection of radioactive contraband.

24. The radiation detection and analysis system of claim 21 wherein the radiation detection and analysis system comprises a radiation detector for subterranean use.

25. The radiation detection and analysis system of claim 21 wherein the plastic matrix comprises nano-scale particles of titanium dioxide in a sufficient amount to increase the refractive index of the plastic matrix to match the refractive index of the scintillation material.

26. The radiation detection and analysis system of claim 21 wherein the plastic matrix comprises at least one of an isotropic thermoplastic resin, an anisotropic thermoplastic resin, an isotropic thermoset resin, or an anisotropic thermoset resin.

27. The radiation detection and analysis system of claim 21 wherein the nano-scale particles of the scintillation material comprise a material selected from the group consisting of metal oxides, metal oxyhalides, metal oxysulfides, metal halides, and combinations thereof.

28. A method for manufacturing a scintillation detector comprises:
coating nano-scale particles with a small molecule ligand comprising trioctylphosphine oxide or trialkoxysilane, wherein the nano-scale particles comprise a scintillation material;
embedding the nano-scale particles in a plastic matrix; and
attaching a photodetector system to the plastic matrix, wherein the photodetector system comprises one or more elements configured to convert photons to electrical signals.

29. The method of claim 28 wherein the plastic matrix comprises at least one of an isotropic thermoplastic resin, an anisotropic thermoplastic resin, an isotropic thermoset resin, or an anisotropic thermoset resin.

30. The method of claim 28 wherein the plastic matrix comprises nano-scale particles of titanium dioxide in an amount sufficient to increase the refractive index of the plastic matrix to match the refractive index of the scintillation material.

31. The method of claim 28 wherein the plastic matrix comprises at least one of polycarbonate, polystyrene, polyurethane, polyacrylate, polyamide, polymethyl pentene, cellulose based polymer, styrene-butadiene copolymer, polyethylene terephthalate (PET), polyethylene terephthalate glycol (PETG), phenol formaldehyde resin, poly N-vinyl carbazole, liquid crystalline polymer (LOP), polysiloxane, polyphosphazene, polyimides, epoxides, phenolic resins, or combinations thereof.

32. The method of claim 28 wherein the nano-scale particles of the scintillator material are less than about 100 nm in size.

33. The method of claim 28 wherein the nano-scale particles of the scintillation material comprise a material selected from the group consisting of metal oxides, metal oxyhalides, metal oxysulfides, metal halides, and combinations thereof.

34. The method of claim 28 wherein the nano-scale particles of the scintillation material comprise at least one phosphor having a general formula of (Y,Gd)2O3:Eu; Y2SiO5:Ce; Y2Si2O7:Ce; LuAlO3:Ce; Lu2SiO5:Ce; Gd2SiO5:Ce; YAlO3:Ce; ZnO:Ga; CdWO4; LuPO4:Ce; PbWO4; Bi4Ge3O12; CaWO4; Gd2O2S:Tb; Gd2O2S:Pr; (RE)3Al5O12:Ce, wherein RE is at least one rare earth metal; or combinations thereof.

35. The method of claim 28 wherein the nano-scale particles of the scintillation material comprise at least one a phosphor having a general formula of LaOX:Tb; wherein X is selected from the group consisting of Cl, Br, I, and combinations thereof.

36. The method of claim 28 wherein the nano-scale particles of the scintillation material comprise a phosphor having the general formula

[La$_{(1-x)}$Ce$_x$][Cl$_{(1-y-z)}$Br$_{(y-z)}$I$z$]$_3$, wherein $0 \geq x \geq 1$;
$0 \geq (1-y-z) \geq 1$; $0 \geq z \geq 1$; and $0 \geq (y-z) \geq 1$.

37. The method of claim 28 wherein the nano-scale particles of the scintillation material comprise a phosphor having a general formula of MXn:Y; wherein M comprises at least one metal ion selected from the group consisting of La, Na, K, Rb, Cs and combinations thereof; X comprises at least one halide ion selected from the group consisting of F, Cl, Br, I, and combinations thereof; Y comprises at least one metal ion selected from the group consisting of Tl, Tb, Na, Ce, Pr, Eu, and combinations thereof; and n is an integer between 1 and 4, inclusive.

38. The method of claim 28 wherein the nano-scale particles of the scintillation material comprise at least one phosphor having a general formula of LaCl3:Ce, RbGd2F7:Ce, CeF3, BaF2, Csl(Na), CaF2:Eu, LiI:Eu, OsI, CsF, CsI:Tl, NaI:Tl, CdS:In, ZnS, or combinations thereof.

39. The scintillator of claim 28 wherein the nano-scale particles of the scintillation material are coated with at least one of plastic resin or an organic compound prior to incorporation into the plastic matrix.

40. The method of claim 28 wherein the one or more photodetectors comprise at least one of photomultiplier tubes, photodiodes, phototransistors, or charge coupled array devices.

41. The method of claim 28 wherein the plastic matrix is formed into separate cells and wherein each of the separate cells is attached to a corresponding element in the one or more elements of the photodetector system.

42. The method of claim 28 wherein the plastic matrix is cut into separate cells and wherein each of the separate cells is attached to a corresponding elements in the one or more elements of the photodetector system.

43. The method of claim 28 wherein the plastic matrix is isotropic, and the isotropic alignment of the plastic matrix generally directs light from the nano-scale particles of the scintillation material toward the one or more photodetectors attached to the plastic matrix.

44. The method of claim 28 wherein the plastic matrix is isotropic and the isotropic alignment of the plastic matrix generally suppresses light transmission in a substantially horizontal direction relative to the surfaces of the one or more photodetectors.

* * * * *

UNITED STATES PATENT AND TRADEMARK OFFICE
CERTIFICATE OF CORRECTION

PATENT NO. : 7,608,829 B2
APPLICATION NO. : 11/728400
DATED : October 27, 2009
INVENTOR(S) : Loureiro et al.

It is certified that error appears in the above-identified patent and that said Letters Patent is hereby corrected as shown below:

On the Face Page, in Field (56), under "OTHER PUBLICATIONS", in Column 2, Line 2, delete "SrAl2O4:Eu2+, Dy3+" and insert -- $SrAl_2O_4:Eu^{2+}, Dy^{3+}$ --, therefor.

On Page 2, Line 34, below "6,707,046" insert -- 6,709,212 B1 3/2004 Craig Lauchner --.

In Column 6, Line 55, delete "Csl," and insert -- CsI, --, therefor.

In Column 7, in Table 1, Line 9, delete "Y2SiO5:Ce" and insert -- $Y_2SiO_5$:Ce --, therefor.

In Column 16, Line 55, in Claim 4, delete "(LOP)," and insert -- (LCP), --, therefor.

In Columns 16 & 17, Lines 67 & 1-4, in Claim 7, delete "(Y,Gd)2O3:Eu; Y2SiO5:Ce; Y2Si2O7:Ce; LuAlO3:Ce; Lu2SiO5:Ce; Gd2SiO5:Ce, YAlO3:Ce; ZnO:Ga; CdWO4; LuPO4:Ce; PhWO4; Bi4Ge3O12; CaWO4; Gd2O2S:Tb; Gd2O2S:Pr; (RE)3Al5O12:Ce," and insert -- $(Y,Gd)_2O_3$:Eu; $Y_2SiO_5$:Ce; $Y_2Si_2O_7$:Ce; $LuAlO_3$:Ce; $Lu_2SiO_5$:Ce; $Gd_2SiO_5$:Ce, $YAlO_3$:Ce; ZnO:Ga; $CdWO_4$; $LuPO_4$:Ce; $PhWO_4$; $Bi_4Ge_3O_{12}$; $CaWO_4$; $Gd_2O_2S$:Tb; $Gd_2O_2S$:Pr; $(RE)_3Al_5O_{12}$:Ce, --, therefor.

In Column 17, Lines 14-15, in Claim 9, delete
" $[La(1-x)Cex][Cl(1-y-z)Br(y-z)Iz]3$; wherein $0 \geqq x \geqq 1$; $0 \geqq (1-y-z) \geqq 1$; $0 \geqq z \geqq 1$; and $0 \geqq (y-z) \geqq 1$. " and insert
-- $[La_{(1-x)}Ce_x][Cl_{(1-y-z)}Br_{(y-z)}I_z]_3$; wherein $0 \leq x \leq 1$; $0 \leq (1-y-z) \leq 1$; $0 \leq z \leq 1$; and $0 \leq (y-z) \leq 1$. --, therefor.

In Column 17, Line 19, in Claim 10, delete "MXn:Y;" and insert -- $MX_n$:Y; --, therefor.

In Column 17, Line 29, in Claim 11, delete "LnX3:Ce," and insert -- $LnX_3$:Ce, --, therefor.

In Column 17, Lines 30-31, in Claim 11, delete "RbGd2F7:Ce; CeF3, BaF2, CsI(Na), CaF2:Eu," and insert -- $RbGd_2F_7$:Ce; $CeF_3$, $BaF_2$, CsI(Na), $CaF_2$:Eu, --, therefor.

In Column 17, Line 31, in Claim 11, delete "OsI, CsF, CsI:Tl, NaI:Tl," and insert -- CsI, CsF, CsI:Tl, NaI:Tl, --, therefor.

In Column 19, Line 16, in Claim 31, delete "(LOP)," and insert -- (LCP), --, therefor.

CERTIFICATE OF CORRECTION (continued)
U.S. Pat. No. 7,608,829 B2

In Column 19, Lines 28-32, in Claim 34, delete "(Y,Gd)2O3:Eu; Y2SiO5:Ce; Y2Si2O7:Ce; LuAlO3:Ce; Lu2SiO5:Ce; Gd2SiO5:Ce; YAlO3:Ce; ZnO:Ga; CdWO4; LuPO4:Ce; PbWO4; Bi4Ge3O12; CaWO4; Gd2O2S:Tb; Gd2O2S:Pr; (RE)3Al5O12:Ce," and insert -- $(Y,Gd)_2O_3$:Eu; $Y_2SiO_5$:Ce; $Y_2Si_2O_7$:Ce; $LuAlO_3$:Ce; $Lu_2SiO_5$:Ce; $Gd_2SiO_5$:Ce; $YAlO_3$:Ce; ZnO:Ga; $CdWO_4$; $LuPO_4$:Ce; $PbWO_4$; $Bi_4Ge_3O_{12}$; $CaWO_4$; $Gd_2O_2S$:Tb; $Gd_2O_2S$:Pr; $(RE)_3Al_5O_{12}$:Ce, --, therefor.

In Column 19, Lines 42-43, in Claim 36, delete "$[La_{(1-x)}Ce_x][Cl_{(1-y-z)}Br_{(y-z)}I_z]_3$; wherein $0 \leq x \leq 1$; $0 \leq (1-y-z) \leq 1$; $0 \leq z \leq 1$; and $0 \leq (y-z) \leq 1$." and insert -- $[La_{(1-x)}Ce_x][Cl_{(1-y-z)}Br_{(y-z)}I_z]_3$; wherein $0 \leq x \leq 1$; $0 \leq (1-y-z) \leq 1$; $0 \leq z \leq 1$; and $0 \leq (y-z) \leq 1$. --, therefor.

In Column 20, Line 3, in Claim 37, delete "MXn:Y;" and insert -- $MX_n$:Y; --, therefor.

In Column 20, Lines 13-14, in Claim 38, delete "LaCl3:Ce, RbGd2F7:Ce, CeF3, BaF2," and insert -- $LaCl_3$:Ce, $RbGd_2F_7$:Ce, $CeF_3$, $BaF_2$, --, therefor.

In Column 20, Line 14, in Claim 38, delete "CsI(Na)," and insert -- CsI(Na), --, therefor.

In Column 20, Line 14, in Claim 38, delete "CaF2:Eu," and insert -- $CaF_2$:Eu, --, therefor.

In Column 20, Lines 14-15, in Claim 38, delete "OsI, CsF, CsI:Tl, NaI:Tl," and insert -- CsI, CsF, CsI:Tl, NaI:Tl, --, therefor.

Signed and Sealed this

Sixteenth Day of March, 2010

David J. Kappos
*Director of the United States Patent and Trademark Office*